United States Patent [19]

Sarantakis et al.

[11] 4,380,535
[45] Apr. 19, 1983

[54] ENKEPHALIN DEGRADING ENZYME INHIBITORS

[75] Inventors: Dimitrios Sarantakis, West Chester; William Dvonch, Radnor, both of Pa.

[73] Assignee: American Home Products Corporation, New York, N.Y.

[21] Appl. No.: 304,731

[22] Filed: Sep. 23, 1981

[51] Int. Cl.³ .................. A61K 37/00; C07C 103/52
[52] U.S. Cl. .............................. 424/177; 260/112.5 E
[58] Field of Search .................. 260/112.5 E; 424/177

[56] References Cited

U.S. PATENT DOCUMENTS 4,127,534 11/1978 Coy et al. .................. 260/112.5 E
4,244,944 1/1981 Wilkinson .................. 260/112.5 E Primary Examiner—Delbert R. Phillips
Attorney, Agent, or Firm—George Tarnowski

[57] ABSTRACT

Compounds which inhibit the brain enzyme degradation of enkephalins and which exhibit their own analgesic effect, having the formula

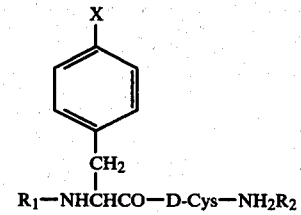

$R_1$—NHCHCO—D-Cys—NH$_2$R$_2$ wherein $R_1$ is hydrogen or lower alkyl; X is hydrogen, hydroxy, halo, nitro, amino or lower alkoxy; $R_2$ is hydrogen or

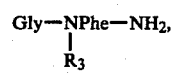

Gly—NPhe—NH$_2$,
       |
       R$_3$ wherein $R_3$ is lower alkyl and $R_4$ is L- or D-Thz or Pro, and the pharmaceutically acceptable salts thereof.

2 Claims, No Drawings

ENKEPHALIN DEGRADING ENZYME INHIBITORS

The identification and synthesis of enkephalins in 1975 and the recognition that the amino acid sequence of methionineenkephalin is present in the pituitary prohormone β-lipotropin has been followed by a phenomenal research effort into brain opiates.

Enkephalin, a natural opiate receptor agonist in the brain, has been identified [see Hughes et al., Nature, 258, 577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). It has been suggested that enkephalin receptors may be sites at which morphine-like drugs exert their analgesic activities, and that enkephalins may act as neurotransmitters in brain systems for pain suppression or analgesia. The administration by injection of methionine-enkephalin and leucine-enkephalin into the brain ventricle in rats induces a profound analgesia that is fully reversible by naloxone [see Belluzzi et al., Nature, 260, 625 (1976)].

However, the enkephalins have a number of limitations on their suitability as pharmacological tools. First, natural enkephalins are inactive when administered peripherally, and it is believed that the enkephalins, in general, are rapidly destroyed by blood enzymes. Second, even the endogenously occurring enkephalins are subject to extremely rapid inactivation in brain tissues following their release and action. Such a result would comport with the similar inactivation of many other neurotransmitters.

Research is in progress to elucidate the nature and structure of the enzyme or enzymes responsible for the inactivation of enkephalins. Evidence exists that an aminopeptidase associated with the membranes carrying the opiate receptors with which the enkephalins interact is involved in the inactivation of enkephalins [see Schnebli et al., Biochimica et Biophysica Acta, 569, 89–98 (1979)]. The inactivation proceeds by the very rapid hydrolysis of the enkephalin Tyr-Gly bond, and this cleavage has been extensively studied [see Hambrook et al., Nature, 262, 782–783 (1976); Meek et al., Neuropharmacology, 16, 151–154 (1977); Marks et al., Biochem. Biophys. Res. Commun., 74, 1552–1559; Guyon et al., Biochem. Biophys. Res. Commun., 88, 919–926 (1979)]. It has been further found that an "enkephalinase" is in all probability responsible for the release of the tripeptide Tyr-Gly-Gly from the enkephalins, and that this "enkephalinase" is a dipeptidyl carboxypeptidase [see Malfroy et al., Nature, 276, 523–526 (1978); Guyon et al., Life Sciences, 25, 1605–1612 (1979); Gorenstein et al., Life Sciences, 25, 2065–2070 (1979)]. Still other types of brain enzymes may be involved in inactivation of endogenous enkephalinic compounds [see Traficante et al., Life Sciences, 26, 1697–1706 (1980)].

The transient effects of the endogenous enkephalins and the consequent attempts to identify and elucidate the brain enzymes which may be responsible for the inactivation of enkephalins has led to efforts to find compounds which will inhibit the effects of the brain enzymes, thereby potentiating the effects of the enkephalins. For example, antibiotics such as puromycin and bacitracin have been shown to be effective inhibitors of the "aminopeptidase"-catalyzed breakdown of enkephalins [see Knight et al., J. of Biol. Chem., 253, 3843–3847 (1978)], as well as certain peptides [see Barclay et al., Biochem. Biophys. Res. Commun., 96, 1732–1738 (1980)], while various naturally-occurring and synthetic peptidic compounds have been shown to inhibit both "aminopeptidase" and "enkephalinase" activity in particulate and soluble fractions from mouse striatum [see Malfroy et al., Nature, 276, 523–526 (1978); Knight et al., J. of Biol. Chem., 253, 3843–3847 (1978); Fournie-Zaluski et al., Biochem. Biophys. Res. Commun., 91, 130–135 (1979); Sullivan et al., Peptides, 1, 31–35 (1980)].

In light of all these findings, it will be highly desirable to have compounds which inhibit the enkephelin-degrading brain enzyme(s) and which can further potentiate the effects of the endogenous enkephalins by exerting their own analgesic effects.

DESCRIPTION OF THE INVENTION

In accordance with the invention, there are now provided compounds which inhibit the brain aminopeptidase degradation of endogenous enkephalins and which also exhibit their own potent analgesic effect, having the formula:

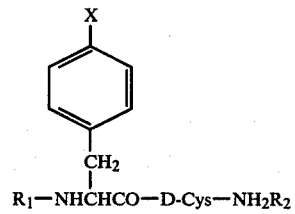

$R_1$—NHCHCO—D-Cys—$NH_2R_2$ wherein $R_1$ is hydrogen or lower alkyl; X is hydrogen, hydroxy, halo, nitro, amino or lower alkoxy; $R_2$ is hydrogen or

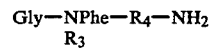

Gly—NPhe—$R_4$—$NH_2$
　　　$R_3$ wherein $R_3$ is lower alkyl and $R_4$ is L- or D-Thz or Pro and the pharmaceutically acceptable salts thereof.

While no mode of action for the compounds of the invention can be advanced with any degree of certitude, it is postulated that they may inhibit some of the brain enzymes which may be implicated in the inactivation of the endogenous enkephalins and perhaps even in the inactivation of the endogenous, α-, β- and δ-endorphins. Moreover, in addition to their postulated enkephalin-degrading enzyme inhibition, the compounds also possess their own analgesic activity. In the context of their postulated mode of action, then, the compounds can be administered by pharmacologically conventional routes to inhibit the enkephalin-inactivating brain enzyme or enzymes, thereby potentiating the effects of the endogenous enkephalins and/or endorphins, and they can be administered in sufficiently high doses to exert their own analgesic effect.

The compounds of the invention, being polypeptides, can be produced by the well known solid phase method as described by Stewart et al., Solid Phase Peptide Synthesis, Freeman and Co., San Francisco, 1969. As applied to some of the compounds of this invention, α-amino protected thiazolidine carboxylic acid is attached to a benzhydrylamine polystyrene resin followed by removal of the α-amino protecting group with trifluoroacetic acid in methylene chloride, trifluoroacetic acid alone or HCl in dioxane. The deprotection is carried out at temperatures between about 0° C. and room temperature. Other standard cleaving reagents and conditions for removal of specific α-amino protecting groups may be used as described in Schroder and Lubke, "The Peptides,"1, 72–72 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., *Analyt. Biochem.*, 34, 595 (1970). Where incomplete coupling has occurred, the reaction is repeated before the α-amino protecting group is removed for introduction of the next amino acid or amino acid sequence. The coupling reagent employed is diisopropylcarbodiimide.

After the desired amino acid sequence has been synthesized, the polypeptide is removed from the resin support by treatment with hydrogen fluoride and anisole to obtain the fully deprotected polypeptide. The polypeptide is then purified by one or more purification techniques, including gel filtration, high pressure preparative liquid chromatography and partition chromatography.

The N-substituted tyrosine and phenylalanine reactants employed in the production of the compounds disclosed herein are readily prepared by reaction of methylchloride, allylchloride, cyclopropylmethylchloride or cyclobutylmethylchloride with a Boc-tyrosyl ester or Boc-phenylalanine ester in the presence of silver oxide. The product is then saponified and hydrolyzed to obtain the desired reactant.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,3-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

Protection for the phenolic hydroxy group of tyrosine may be benzyl, 2,6-dichlorobenzyl, benzyloxycarbonyl, 2-bromobenzyloxycarbonyl and the like.

The protecting group for the sulfhydryl group of the cysteinyl amino acid residue is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc.); trityl, benzyloxycarbonyl, benzhydryl, p-methoxybenzyloxycarbonyl, benzylthiomethyl, ethylcarbamoyl, thioethyl, tetrahydropyranyl, acetamidomethyl; benzoyl, s-sulfonate salt, etc.

In selecting a particular side-chain protecting group to be used in the synthesis of the peptides of this invention, the following rules should be followed: (a) the side-chain protecting group must be stable to the reagent and under the reaction conditions selected for removing the α-amino protecting group at each step of the synthesis, (b) the protecting group must retain its protecting properties (i.e. not be split off under coupling conditions), and (c) the side-chain protecting group must be removable upon the completion of the synthesis containing the desired amino acid sequence under reaction conditions that will not alter the peptide chain.

The pharmaceutically acceptable salts of the compounds used in the invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts," and include the sodium, potassium, ammonium, and lower alkylamine salts. The salts are prepared and isolated by conventional methods.

In carrying out the method of this invention the active compound can be administered either alone or in combination with inert pharmaceutically acceptable carriers in a variety of dosage forms, orally or parenterally. The dose requirements will vary with the severity of the pain, the animal being treated, the compound employed or the dosage form employed. Therapy is instituted at low dosages and the dosage is increased incrementally until the desired analgesic effect is achieved.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportions of the active ingredient in a dosage form must be sufficient to impart analgesic activity thereto.

The ability of the compounds of the invention to inhibit the enkephalin-degrading activity of brain enzymes and the analgesic effect of the compounds of the invention is demonstrated in the test procedures and assays which follow the below presented preparatory examples.

EXAMPLE 1

$N^\alpha$-t-butyloxycarbonyl-$N^\alpha$-methyl-0-2,6-dichlorobenzyl-L-tyrosyl-S-p-methoxy-benzyl-D-cysteinyl-glycyl-N-methyl-L-phenylalanyl-L-thiazolidine-4-carboxybenzhydryl polystyrene 8 g. (0.4 meq/g of available amino) of benzhydrylamine polystyrene resin (Bachem groups Inc.) is placed in the reaction vessel of a Beckman 990A Peptide Synthesizer and subjected to subsequent cycles of amino acid deprotection and amino acid couplings as described in programs 1 and 2, the latter being performed to secure complete coupling of each amino acid. The following amino acids are incorporated onto the benzhydrylamine resin: Boc-Thz-OH, Boc-N-Me-Phe-OH, Boc-Gly-OH, Boc-D-Cys (SMOB), and Boc-N-Me-Tyr(Cl$_2$Bzl)OH to yield the title peptidoresin.

Program 1

1. Wash with CH$_2$Cl$_2$×3.
2. Treat with TFA-CH$_2$Cl$_2$-EDT, 1:1:5% for 5 min.
3. Repeat (2) for 25 minutes.
4. Wash with CH$_2$Cl$_2$×4.
5. Treat with TEA 12% in DMF for 1 minute.
6. Repeat (5) for 5 minutes.
7. Wash with CH$_2$Cl$_2$×3.
8. Add 4 equivalents of Boc-protected amino acid and stir for 5 minutes.
9. Add 2 equivalents of 1M-DIC solution in DMF and stir for 25 minutes.
10. Add 2 equivalents of 1M-DIC solution in DMF and stir for 180 minutes.
11. Wash with CH$_2$Cl$_2$×3.
12. Wash with methanol ×3.
13. Wash with CH$_2$Cl$_2$×3.

Program 2

1. Wash with CH$_2$Cl$_2$×3.
2. Add 2 equivalents of Boc-protected amino acid and stir for 5 minutes.
3. Add 2 equivalents of 1M-DIC solution in DMF and stir for 180 minutes.
4. Wash with DMF ×3.
5. Wash with CH$_2$Cl$_2$×3.
6. Wash with methanol ×3.
7. Wash with CH$_2$Cl$_2$×3.

EXAMPLE 2

N$^\alpha$-Methyl-L-tyrosyl-D-cysteinyl-glycyl-N-methyl-L-phenylalanyl-L-thiazolidine-4-carboxamide, acetate salt The peptidoresin of the previous example is treated with 200 ml liquid anhydrous HF in the presence of 20 ml anisole for 60 minutes in an ice-bath and under exclusion of air. The excess HF is removed under vacuo as fast as possible (ca. 1 hour) and the residue is taken in 10% aqueous AcOH (ca. 200 ml) treated with Amberlite IR-45 (acetate form) filtered and lyophilized to yield 840 mg of crude material. This material is chromatographed through a column of Sephadex G10 (2.5×90 cm) and eluted with 5% aqueous AcOH. The material which emerges in fractions (5 ml each) 60 to 87 is pooled and lyophilized to yield 650 mg of the title compound.
TLC silica gel precoated glass plates.
R$_f$ (n-BuOH—H$_2$O—AcOH, 4:1:1, v/v) 0.45. Avicel precoated glass plates.
R$_f$ (system as above) 0.75.
Amino acid analysis: N-Me-Tyr (1) 0.83, Gly (1) 1, Cys ND, Thioproline, ND, N-Me-Phe (1) 0.83.

EXAMPLE 3

The ability of the compounds of the invention to inhibit the brain enzyme degradation of enkephalins was studied in the following test procedure.
Brain enzymes from rats are used in the procedure and for this purpose solubilized rat brain membrane preparation, prepared as follows, is used:
Brains from young male Charles River Co. rats were homogenized in 30 volumes 50 mM Tris pH 7.7 with a Polytron (Brinkmann). The homogenate was centrifuged at 50,000 x g for 15 min. The supernatant was discarded the pellet resuspended in 50 mM Tris pH 7.7 and centrifuged at 50,000 x g for 15 min. The resultant pellet was resuspended, centrifuged and washed 3 additional times as described above. The membrane pellet was solubilized by resuspension in 15 volumes 50 mM Tris pH 7.7, 1% Triton X-100 and incubation at 37° C. for 45 min. Solubilized enzymes were obtained after centrifugation at 100,000 x g for 60 min.

This preparation is incubated at 37° C. for 1 hour in the presence of $5.0 \times 10^{-4}$M $^3$H-Leu-enkephalin in 50 mM tris buffer and $1.0 \times 10^{-3}$M of the inhibitor to be tested. The reaction is terminated by the addition of 10 μl of 1NHCl (200 μl hydrolysis volume) and heating 5 minutes at 100° C. The reaction mixture is spotted onto a thin-layer chromatography (TLC) plate of silica gel. Chromatography is carried out in the system n-butanol: ethyl acetate: acetic acid: water (1:2:1:1). Compounds are visualized with ninhydrin spray. Markers of Leu-enkephalin (LE), tyrosinge (T) and tyrosine-glycine-glucine (TGG) are run with all samples and the relevant areas are scraped into scintillation vials and counted. R$_f$ values in this TLC system are TGG=0.24, T-0.34 and LE=0.52.

When N-Me-Tyr-D-Cys-Gly-N-MePhe-Thz-NH$_2$ is tested in this procedure, the percentage of hydrolysis poructs (analyzed by TLC of tagged Leu-enkephalin) is as follows:

|  | Tyr |
|---|---|
| Control | 52% |
| Compound | 14% |

These results show that the compound tested exhibited quite potent inhibition of enkephalin-degrading aminopeptidase.

EXAMPLE 4

The analgesic activity of the compounds of the invention is demonstrated following a modification of phenylbenozquinone-induced writhing test procedure of Siegmund et al., *Proc. Soc. exp. Biol. Med.*, 95, 729–731 (1957). According to this procedure, test compound is administered at various doses to ten mice per dose level. The animals then receive intraperitoneal injection with 0.25 ml of the writhing agonist (a 0.02% solution of benzoquinone) 5 min before the beginning of a preselected, 10 min observation period. Typical observation periods include 10 to 20, 25 to 35, 40 to 50 and 55 to 65 min following administration of the test compound. The mice are observed during the observation period for the presence of an all-or-none writhing reaction. Animals which fail to writhe during the observation period are considered to exhibit an antinociceptive effect. The ratio of responding (animals exhibiting an antinociceptive effect) mice to dosed mice is determined for each dose of the test compound.

If the compound is active, its dose response and ED$_{50}$ value are determined according to the method of D. J. Finney (*Statistical Methods in Biological Assay*, Griffin and Co., London, 1964).

When tested according to the above procedure, the compound N-Me-Tyr-D-Cys-Gly-N-MePhe-Thz-NH$_2$ was found to be active, with an ED$_{50}$ of 18 mg/kg (10.9–29.7) at 15 minutes by subcutaneous administration.

EXAMPLE 5

The compounds of the invention are tested for their opiate receptor affinities relative to morphine according to a modification of the procedure of Chang et al., *Life Sciences*, 18, 1473–83 (1976).

According to this procedure, a fasted male Charles River CD rat, 190–290 g, is killed with a guillotine after ether anesthesia, and the brain is rapidly removed. The cerebellum is excised and the brain is homogenized in 100 vol. (usually 150 ml) iced 0.05 M Trizma buffer (pH 7.4 at 25°) in a Brinkman Polytron for 1 min. at setting 3. The homogenate is centrifuged at 49,500 g for 15 min. (Sorvall SS-34 rotor at 19,500 rpm) in 50 ml propylene tubes. The supernatant is decanted, and the pellets are resuspended in iced buffer to original volume by use of a motor driven pestle tissue grinder (50 ml size; 10 double strokes). The homogenate is centrifuged again and resuspended in 10 ml iced buffer.

For the assay, 0.10 ml of this iced homogenate is added to 12×75 mm glass tubes filled according to the following protocol (final total volume: 0.50 ml):

|  | Sodium Chloride (0.050ml 1M NaCl) | Sample (0.050ml) | Morphine (0.050ml of $2 \times 10^{-2}$ M) | Buffer (ml) |
|---|---|---|---|---|
| Control (6 tubes) | + | − | − | 0.30 |
| Sample (9 conc: 4 tubes) | + | + | − | 0.25 |
| Carrier (6 tubes) | + | − | + | 0.25 |

The filled tubes are equilibrated for 5 min. at room temperature, iced, and $^3$H-naloxone (0.050 ml of $1.3 \times 10^{-8}$M; 20 Ci/mmol) is added to all tubes.

The assay tubes are mechanically shaken for an incubation time of 30 min. at 4° C. The contents are filtered under reduced pressure through Whatman glass-fiber circles (GF/B, 2.4 cm dia.). The filters are washed twice with 8 ml cold buffer, placed in scintillation vials, and 12 ml of Hydromix (Yorktown Research) or equivalent are added to each vial. The vials are let stand at room temperature for 6 hours with intermittent hand shaking before loading into the counter and are equilibrated in the counter for 80 min. before counting one time for 1 min.

The assay is calculated as follows:

| Control (specific + non-specific binding) − Carrier (non-specific binding) | Sample (specific ± non-specific binding) − Carrier |
|---|---|
| net control = 100% binding | net sample |

$$100 \times \frac{\text{net sample}}{\text{net control}} = \% \text{ control binding}$$

The data is plotted as % control binding vs. log concentration sample to obtain the concentration that displaces 50% of the $^3$H-naloxone (ID$_{50}$). Comparisons are made with morphine as a standard to obtain relative displacement potencies. Assays are run twice for each sample on different days. Displacement is exhibited by both opiate agonists and antagonists.

The compound N-Me-Tyr-D-Cys-Gly-N-MePhe-Thz-NH$_2$, when tested according to the above procedure, showed a relative displacement potency of 2.6 as compared to morphine (1).

What is claimed is:

1. A method for inhibiting brain enzyme degradation of enkephalins which comprises administering to a mammal an amount sufficient to inhibit the brain enzyme degradation of said enkephalins of a compound of the formula:

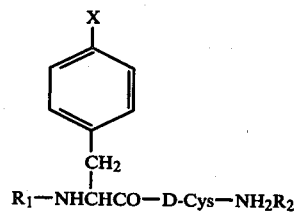

wherein R$_1$ is hydrogen or lower alkyl; X is hydrogen, hydroxy, halo, nitro, amino or lower alkoxy; R$_2$ is hydrogen or $$\text{Gly—NPhe—R}_4\text{—NH}_2,$$
$$\text{|}$$
$$\text{R}_3$$

wherein R$_3$ is lower alkyl and R$_4$ is L- or D-Thz or Pro and the pharmaceutically acceptable salts thereof.

2. The method of claim 1 wherein said compound is N-Me-Tyr-D-Cys-Gly-N-MePhe-Thz-NH$_2$.

* * * * *